(12) United States Patent
Mao

(10) Patent No.: US 10,188,803 B2
(45) Date of Patent: Jan. 29, 2019

(54) DISPOSABLE SAFE VEIN TRANSFUSION PUNCTURE NEEDLE

(71) Applicant: GEMTIER MEDICAL (SHANGHAI) INC., Shanghai (CN)

(72) Inventor: Yaling Mao, Shanghai (CN)

(73) Assignee: GEMTIER MEDICAL (SHANGHAI) INC., Shanghai (CN)

( * ) Notice: Subject to any disclaimer, the term of this patent is extended or adjusted under 35 U.S.C. 154(b) by 0 days.

(21) Appl. No.: 15/312,581

(22) PCT Filed: Apr. 1, 2015

(86) PCT No.: PCT/CN2015/075658
§ 371 (c)(1),
(2) Date: Nov. 18, 2016

(87) PCT Pub. No.: WO2016/062016
PCT Pub. Date: Apr. 28, 2016

(65) Prior Publication Data
US 2017/0216535 A1    Aug. 3, 2017

(30) Foreign Application Priority Data

Oct. 24, 2014  (CN) .......................... 2014 1 0577644
Oct. 24, 2014  (CN) ...................... 2014 2 0621938 U

(51) Int. Cl.
*A61M 5/32*      (2006.01)
*A61M 25/06*    (2006.01)
*A61M 5/158*    (2006.01)

(52) U.S. Cl.
CPC .......... *A61M 5/3245* (2013.01); *A61M 5/158* (2013.01); *A61M 5/3271* (2013.01); *A61M 25/06* (2013.01)

(58) Field of Classification Search
CPC .. A61M 5/3245; A61M 5/3271; A61M 25/06; A61M 5/158
See application file for complete search history.

(56) References Cited

U.S. PATENT DOCUMENTS 4,804,372 A  *  2/1989  Laico ................. A61M 5/3243
                                                        604/198
5,573,512 A  *  11/1996 van den Haak .... A61M 5/3243
                                                        604/110
(Continued)

FOREIGN PATENT DOCUMENTS

CN            2803403          8/2006
CN          103977475         8/2014
(Continued)

OTHER PUBLICATIONS

PCT Search Report dated Jul. 9, 2015 for corresponding PCT International Application No. PCT/CN2015/075658, 3 pages.
(Continued)

*Primary Examiner* — Lauren P Farrar
(74) *Attorney, Agent, or Firm* — Lee & Hayes, PC

(57) ABSTRACT

A disposable safe vein transfusion puncture needle comprising a needle head (4), a needle base (3), a needle sheath sleeved on the needle head (4), and a hose (6) communicated with the needle base (3), and further comprising a plurality of slidable components (1, 2) and a plurality of limiting mechanisms (11, 12, 13, 21, 31, 32), wherein the needle base (3) is in a tubular shape, with one end stationary and communicated with the needle head (4) and the other end connected to the hose (6); each of the slidable components (1, 2) is in a tubular shape and has two open ends, the plurality of slidable components (1, 2) are sleeved on one another, the innermost slidable component (1) is movably sleeved onto the needle base (3), and a sum of lengths of the plurality of slidable components (1, 2) in a moving direction (Continued)

is longer than the length of the needle head (4); the limiting mechanisms (11, 12, 13, 21, 31, 32) are disposed on the plurality of slidable components (1, 2) as well as on the needle base (3). By providing a plurality of slidable components (1, 2) sleeved on the needle base (3) in a layered manner, the operating portion length of the disposable safe vein transfusion puncture needle is made shorter, and by unfolding the slidable components (1, 2) layer by layer so as to shield the needle head (4) during use and after use, the safety level is increased and the pain suffered by the patient is alleviated.

6 Claims, 4 Drawing Sheets

(56) References Cited

U.S. PATENT DOCUMENTS

| | | | | |
|---|---|---|---|---|
| 7,060,053 | B2 | 6/2006 | Nakashima | |
| 2004/0122351 | A1* | 6/2004 | Hamazaki | A61N 5/1007 604/27 |
| 2013/0006189 | A1* | 1/2013 | Tsals | A61M 5/158 604/192 |

FOREIGN PATENT DOCUMENTS

| | | |
|---|---|---|
| CN | 104288866 | 1/2015 |
| CN | 204181959 | 3/2015 |
| JP | 4654102 | 4/2007 |
| JP | 2003265610 | 8/2010 |
| KR | 100800426 | 2/2008 |

OTHER PUBLICATIONS

Chinese Office Action for corresponding Chinese Patent Application No. 20140577644.7 dated Feb. 28, 2015, 8 pages.
PCT International Preliminary Report on Patentability (English translation) for corresponding PCT International Patent Application No. PCT/CN2015/075658 dated Apr. 4, 2017, 6 pages.
JP Notification of Reasons for Refusal for corresponding Japanese Patent Appication No. 2016-562951 dated Aug. 24, 2017, 4 pages.
Korean First Office Action for corresponding Korean Patent Application No. 10-2016-7022824 dated May 9, 2017, 6 pages.
Korean Second Office Action for corresponding Korean Patent Application No. 10-2016-7022824 dated May 9, 2018, 4 pages.
Euroasion First Office Action for corresponding Russion Patent Application No. 201691849/31 dated Mar. 21, 2018, 6 pages.
PCT Written Opinion (English translation) for corresponding PCT International Application No. PCT/CN2015/075658 dated Jan. 19, 2017, 10 pages.

\* cited by examiner

DISPOSABLE SAFE VEIN TRANSFUSION PUNCTURE NEEDLE

The present invention claims the priority rights of Chinese patent applications CN201410577644.7 and CN201420621938.0 filed on Oct. 24, 2014, the entire disclosures of which are incorporated herein by reference.

TECHNICAL FIELD

The present invention relates to an intravenous needle, and in particular relates to a disposable safe vein transfusion puncture needle.

BACKGROUND OF THE INVENTION

Currently, commonly used disposable intravenous needles need to be sleeved with a needle sheath before use, so as to protect the needle head from being bent or bumped. During use, when the needle sheath is removed, a risk of puncture wound is easily caused. But the real danger is at the disposing stage after a transfusion is completed, when the needle has been pulled out from inside a body of a patient that has received transfusion, for discard disposal of the needle, the needle is put into a special disposal box or covered with a needle sheath, and as a result, a risk of puncture wound is easily caused, which might leads to serious consequences such as infection suffered by the medical staff.

In order to deal with such defect, some intravenous needle utilizes a technical means of retractable needle, wherein, after a transfusion is completed, by using an elastic force of a structure such as a spring, the needle head retracts into a protection sheath for protecting the needle head. As such, although the needle head is effectively protected and the medical staff is prevented from being wounded by puncture, however, a great deal of pain is suffered by the patient because of the mechanical motion of the retraction of the needle head.

On the other hand, when the retractable needle retracts, because the retractable mechanical structure thereof usually has gaps which might nip the skin of the patient, more pain might be suffered by the patient.

SUMMARY OF THE INVENTION

A technical problem to be solved by the present invention is that the intravenous needles of prior art have safety issue and the mechanical motion thereof causes pain suffered by the patient, so as to overcome the defects of prior art and provide a disposable safe vein transfusion puncture needle which has a better safety level and causes less pain during mechanical motion.

The above-mentioned technical problem is solved by the following technical solution of the present invention:

A disposable safe vein transfusion puncture needle comprising a needle head, a needle base, a needle sheath sleeved on the needle head, and a hose communicated with the needle base, wherein, the disposable safe vein transfusion puncture needle further comprises a plurality of slidable components and a plurality of limiting mechanisms, the needle base is in a tubular shape with one end stationary and communicated with the needle head and the other end connected to the hose;

each of the slidable components is in a tubular shape and has two open ends, the plurality of slidable components are sleeved on one another, the innermost slidable component is movably sleeved onto the needle base, and a sum of lengths of the plurality of slidable components in a moving direction is longer than the length of the needle head;

the limiting mechanisms are disposed on the plurality of slidable components as well as on the needle base and adapted for securing the innermost slidable component to the needle base as well as securing the plurality of slidable components to one another when the plurality of slidable components slide to completely shield the needle head.

Herein, the hose is a flexible hose for transfusing blood or transfusing liquid that is commonly used in the art. That is to say, before use, a plurality of slidable components are sleeved on the needle base in a layered manner, which is a retracted state, and the needle head is exposed, a needle sheath may sleeve onto the needle head to shield the needle head. During use, the needle sheath is removed and blood transfusion is performed, and after that, in the process of pulling out the needle head, the plurality of tubular slidable components slide to unfold, and are secured in an end-to-end manner by the limiting mechanisms provided on the slidable components and on the needle base, so as to shield the needle head and prevent the needle head from wounding the operator or the patient. As such, when pulling out the needle head, it not only ensures safety, but also avoids pain caused by sudden retraction of the needle head in prior art.

Furthermore, since the operating portion length (the length of components including the needle base and excluding the hose) of an intravenous needle is at least the length of the needle head plus the length of the needle base, and the length of the needle head is a standard length which cannot be altered, therefore, the length design of the needle base becomes the key that determines the operating portion length of an intravenous needle. In the present invention, by utilizing a structure of multiple slidable components sleeved on one another in a layered manner, in a retracted state (when the needle head is completely exposed), compared to using only one slidable component, the layered structure of multiple slidable components can significantly reduce the design length of the needle base.

Preferably, the disposable safe vein transfusion puncture needle comprises a first slidable component movably sleeved on the needle base, and a second slidable component movably sleeved on the first slidable component.

Preferably, the limiting mechanisms comprise one first elastic washer, two second elastic washers, and two third elastic washers, the first elastic washer is circumferentially attached to an interior wall of one end of the first slidable component close to the hose, and an edge of the first elastic washer is smoothly attached to the interior wall of the first slidable component;

the two second elastic washers are sleeved and attached to the needle base, the second elastic washers are adapted for engaging with the first elastic washer when the first slidable component and the second slidable component slide to completely shield the needle head or when the needle head is completely exposed, so as to limit the movement of the first slidable component;

the third elastic washers are respectively circumferentially disposed on an exterior wall of the other end of the first slidable component away from the hose as well as circumferentially attached to an interior wall of one end of the second slidable component close to the hose, the third elastic washers are adapted for engaging with each other when the first slidable component and the second slidable component slide to completely shield the needle head or when the needle head is completely exposed, so as to limit the movement of the second slidable component.

Preferably, the limiting mechanisms comprise two elastic fasteners and four grooves, one of the elastic fasteners is disposed on the first slidable component, and the other elastic fastener is disposed on the second slidable component;

two of the grooves are disposed on the needle base, and the other two grooves are circumferentially disposed on an exterior wall of the first slidable component;

the elastic fasteners and the grooves are adapted for engaging with each other when the first slidable component and the second slidable component slide to completely shield the needle head or when the needle head is completely exposed, so as to limit the movement of the first slidable component and the second slidable component.

Preferably, the first slidable component also has an elastic locking member adapted for stretching out to prevent the second slidable component from sliding back towards the hose when the first slidable component and the second slidable component slide to completely shield the needle head.

Herein, when the first slidable component and the second slidable component unfold, it needs to be ensured that the needle head is not exposed, so the locking steadiness between the two slidable components is directly related to the use safety of the intravenous needle. Therefore, an elastic locking member that can stretch out is provided on the exterior wall of the first slidable component. When the second slidable component has unfolded along the first slidable component to a preset position, the elastic locking member stretches out, and as a result, if the second slidable component has a tendency to slide back, the elastic locking member would push against an edge portion of the second slidable component, rendering it unable to slide back.

Preferably, one end of the second slidable component close to the hose has a smooth projection portion circumferentially disposed thereon. This smooth projection portion is adapted for prevent human skin from getting nipped into the gap between the first slidable component and the second slidable component when the needle head is being inserted into human body.

Herein, because the slidable components and the needle base are sleeved by sliding, there are gaps between the slidable components as well as between the slidable component and the needle base. These gaps tend to nip the skin of the patient during operation, causing pain suffered by the patient. By providing the projection portion, the projection portion would press the skin of the patient during operation to make the skin slightly recessed, so that the skin adjacent to the part that touches the projection portion is prevented from touching the connecting portion with gaps between the first slidable component and the second slidable component as well as between the first slidable component and the needle base, thereby making the skin not easy to be nipped by the gap.

Preferably, a smooth planar surface is disposed on a lateral side of the second slidable component, and the plane of the smooth planar surface forms an angle of 5°-20° with an axial line of the needle head.

Preferably, the second slidable component has a notch disposed on the lateral side with the smooth planar surface, and the notch is in a plane parallel to an axial line of the needle head, one end of the notch extends to an open end of the second slidable component away from the hose, and the other end of the notch extends to intersect with the smooth planar surface.

Herein, in the unfolding process of the first slidable component and the second slidable component, the needle head is required to be kept as close as possible to the skin of the patient, therefore, if the diameters of the first slidable component and the second slidable component are too large, such requirement cannot be met. By providing the smooth planar surface on the second slidable component, the needle head can be placed close to the skin in the unfolding process of the first slidable component and the second slidable component. By providing the notch at a position where the smooth planar surface extends close to the axial line of the needle head, the requirement of the needle head being close to the skin can be further met, thereby alleviating the pain suffered by the patient. Meanwhile, in order to prevent the needle head from accidentally wounding the operator during or after operation, the needle head should not be placed too close to the notch.

Preferably, the notch is located at a preset distance from an axial line of the needle head.

Preferably, the disposable safe vein transfusion puncture needle further comprises a handle, wherein, the second slidable component is provided with at least one antiskid area thereon;

the slidable components are made of elastic material, the elastic fastener is integrally formed in one piece with the slidable component, and the grooves are integrally formed in one piece with the needle base;

the handle is secured to one end of the needle base connected to the hose;

the limiting mechanisms further comprise at least one stopper member disposed on the first slidable component or the needle base, adapted for preventing the second slidable component or the first slidable component from sliding off under a pulling force after the groove is engaged with the elastic fastener.

Herein, the stopper member can further prevent the slidable components and the needle base from sliding off. The stopper member may be any barrier structure, for instance, annular stopper rings are provided on an exterior wall of one end of the needle base close to the needle tip and on an exterior wall of one end of the first slidable component close to the needle tip, two protrusions are respectively provided on an interior wall of one end of the first slidable component close to the hose and on an interior wall of one end of the second slidable component close to the hose, so that the two protrusions on the interior walls of the first and second slidable components are clamped on the annular stopper rings after unfolding.

The beneficial improvement effects of the present invention are: by providing a plurality of slidable components sleeved on the needle base in a layered manner, the operating portion length of the disposable safe vein transfusion puncture needle is made shorter, and by unfolding the slidable components layer by layer so as to shield the needle head during use and after use, the safety level is increased and the pain suffered by the patient is alleviated.

DETAILED DESCRIPTION OF EMBODIMENTS

The present invention is further described through embodiments. However, the present invention is not thereby restricted to the scope of the described embodiments.

Figure 1:
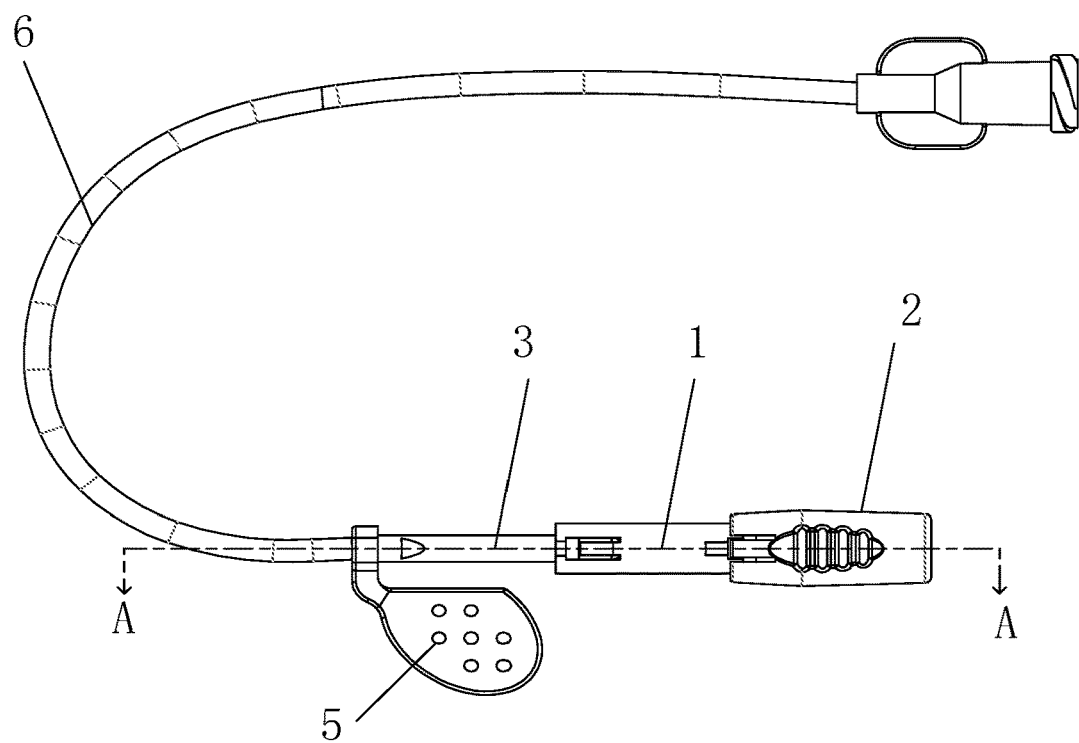
FIG. 1 is a plan view of the disposable safe vein transfusion puncture needle in an unfolded state in a preferable embodiment of the present invention.
Figure 2:
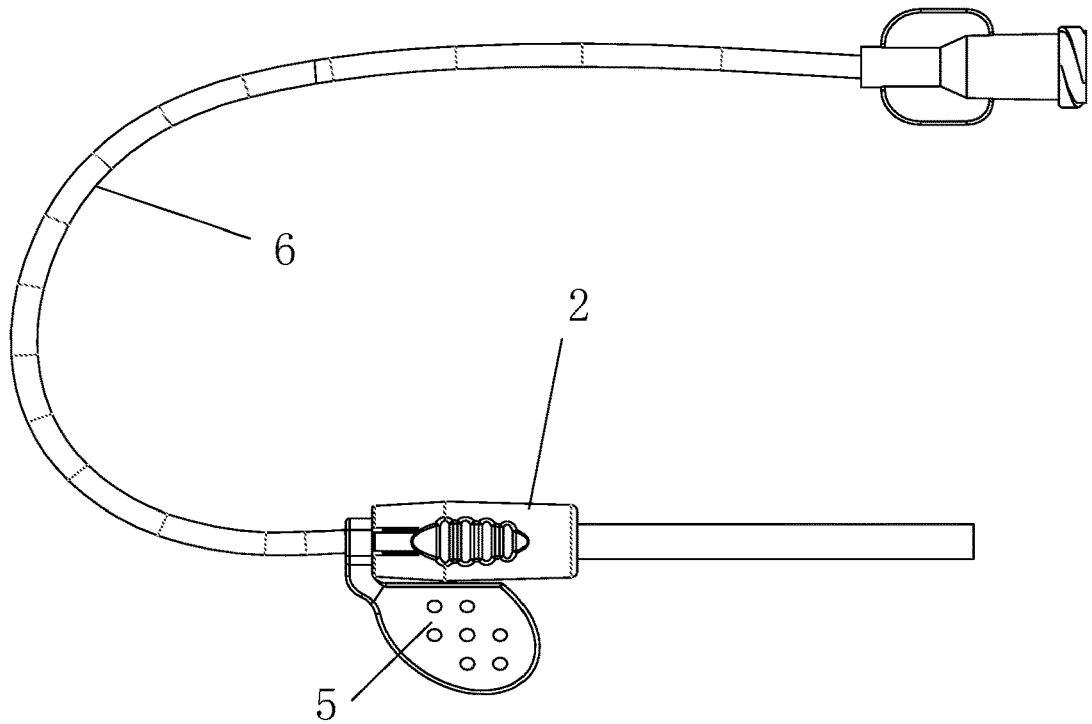
FIG. 2 is a plan view of the disposable safe vein transfusion puncture needle in a retracted state in a preferable embodiment of the present invention.

FIG. 1 is a plan view of the disposable safe vein transfusion puncture needle in an unfolded state in this embodiment of the present invention, and FIG. 2 is a plan view of the disposable safe vein transfusion puncture needle in a retracted state in this embodiment of the present invention. As shown in FIG. 1 and FIG. 2, the disposable safe vein transfusion puncture needle involved in this embodiment comprises a needle head 4, a needle base 3, a needle sheath sleeved on the needle head 4, and a hose 6 communicated with the needle base 3, wherein, the needle base 3 is in a tubular shape with one end stationary and communicated with the needle head 4 and the other end connected to the hose 6.

Figure 3:
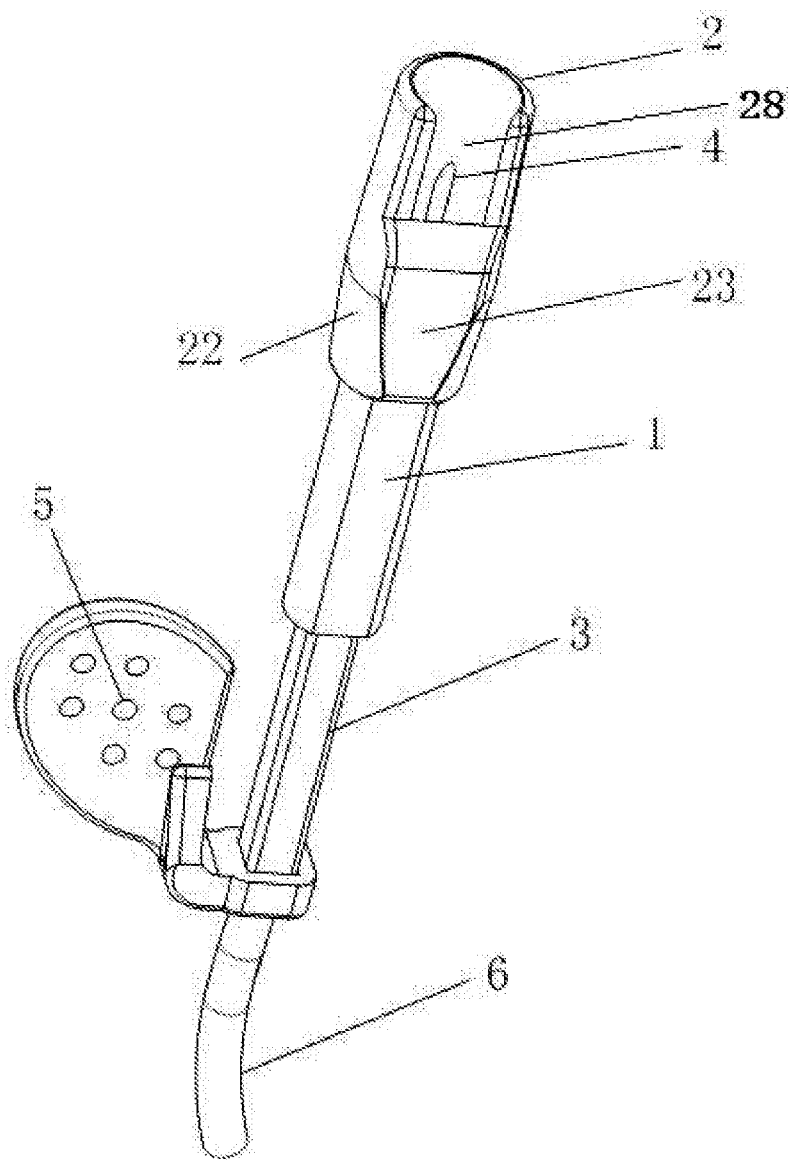
FIG. 3 is a structural diagram of the disposable safe vein transfusion puncture needle in a preferable embodiment of the present invention.
Figure 4:
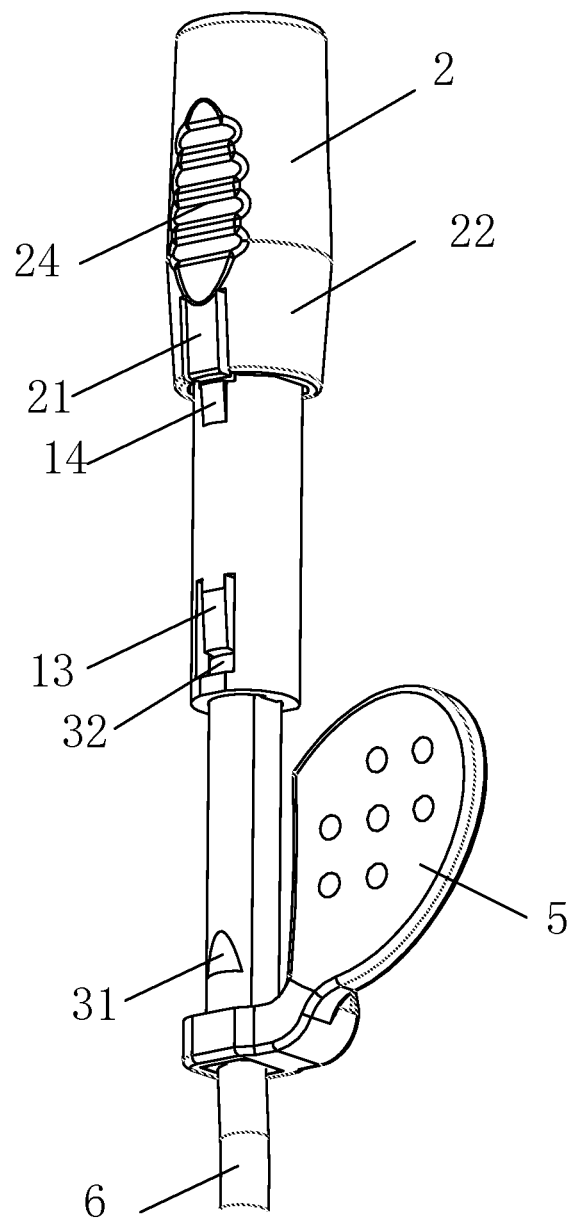
FIG. 4 is another structural diagram of the disposable safe vein transfusion puncture needle in a preferable embodiment of the present invention.
Figure 5:
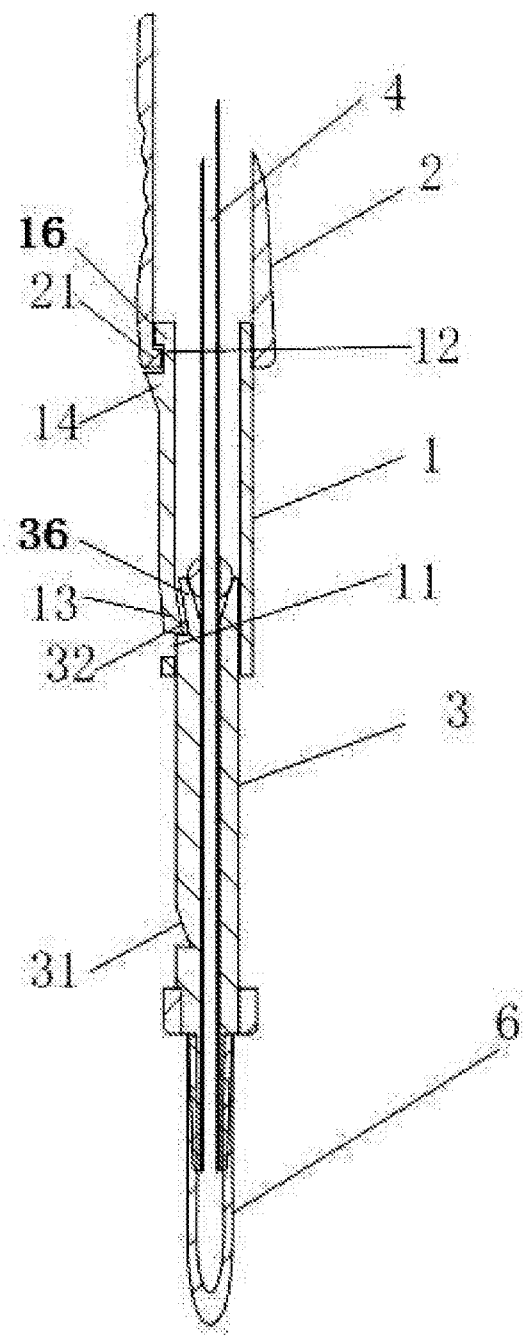
FIG. 5 is a sectional view along the A-A line in FIG. 1.

FIG. 3 and FIG. 4 are structural diagrams of the disposable safe vein transfusion puncture needle in a preferable embodiment of the present invention, and FIG. 5 is a sectional view along the A-A line in FIG. 1. As shown in FIG. 3, FIG. 4 and FIG. 5, the disposable safe vein transfusion puncture needle involved in this embodiment further comprises a slidable component 1 movably sleeved on the needle base 3, and a slidable component 2 movably sleeved on the slidable component 1.

Both of the slidable component 1 and the slidable component 2 are in a tubular shape with two open ends and are sleeved together. The innermost slidable component 1 is movably sleeved onto the needle base 3, and a sum of lengths of the slidable component 1 and the slidable component 2 in a moving direction is longer than the length of the needle head 4.

An elastic fastener 13, an elastic fastener 21 and a groove 31, a groove 32, a groove 11, a groove 12 are provided as limiting mechanisms on the needle base 3, the slidable component 1 and the slidable component 2. When the slidable component 1 and the slidable component 2 is in a unfolded state or in a retracted state, the elastic fasteners and the grooves are adapted for engaging with each other so as to secure the slidable component 1, the slidable component 2 and the needle base 3 to one another.

Wherein, the groove 31 and the groove 32 are disposed on the needle base 3, the elastic fastener 13 is disposed on the slidable component 1, the groove 11 and the groove 12 are disposed on an exterior wall of the slidable component 1, and the elastic fastener 21 is disposed on the slidable component 2. The elastic fastener 13, the elastic fastener 21, and the groove 31, the groove 32, the groove 11, the groove 12 are adapted for engaging with each other when the slidable component 1 and the slidable component 2 slide to completely shield the needle head 4 or when the needle head 4 is completely exposed, so as to limit the movement of the slidable component 1 and the slidable component 2.

An elastic locking member 14 is also provided on the slidable component 1. This elastic locking member 14 is adapted for stretching out to prevent the slidable component 2 from sliding back towards the hose 6 when the slidable component 1 and the slidable component 2 slide to completely shield the needle head 4.

One end of the slidable component 2 close to the hose 6 has a smooth projection portion 22 circumferentially disposed thereon. This smooth projection portion 22 is adapted for prevent human skin from getting nipped into the gap between the slidable component 1 and the slidable component 2 when the needle head 4 is being inserted into human body.

Because the slidable component 1, the slidable component 2 and the needle base 3 are sleeved by sliding, there are gaps between the slidable component 1 and the slidable component 2 as well as between the slidable component 1 and the needle base 3. These gaps tend to nip the skin of the patient during operation, causing pain suffered by the patient. By providing the projection portion 22, the projection portion 22 would press the skin of the patient during operation to make the skin slightly recessed, so that the skin adjacent to the part that touches the projection portion 22 is prevented from touching the connecting portion with gaps between the slidable component 1 and the slidable component 2 as well as between the slidable component 1 and the needle base, thereby making the skin not easy to be nipped by the gap.

A smooth planar surface 23 is disposed on a lateral side of the slidable component 2, and the plane of the smooth planar surface 23 forms an angle of 5° with an axial line of the needle head 4. The slidable component 2 has a notch 28 disposed on the lateral side with the smooth planar surface 23, and the notch 28 is in a plane parallel to the axial line of the needle head 4, one end of the notch 28 extends to an open end of the slidable component 2 away from the hose 6, and the other end of the notch 28 extends to intersect with the smooth planar surface 23. The distance between the notch 28 and the axial line of the needle head 4 is 0.5 mm.

The disposable safe vein transfusion puncture needle involved in this embodiment further comprises a handle 5, wherein, the slidable component 2 is provided with at least one antiskid area 24 thereon (see FIG. 4); the slidable component 1 and the slidable component 2 are made of elastic material, the elastic fasteners are integrally formed in one piece with the slidable component 1 and with the slidable component 2, and the groove 32 are integrally formed in one piece with the needle base 3; the handle 5 is secured to one end of the needle base 3 connected to the hose 6.

Before use, the slidable component 1 and the slidable component 2 are sleeved on the needle base in a layered manner, which is a retracted state, and the needle head 4 is exposed, a needle sheath can be sleeved onto the needle head 4 to shield the needle head. During use, the needle sheath is removed and blood transfusion is performed, and after that, in the process of pulling out the needle head 4, the slidable component 1 and the slidable component 2 slide to unfold, and are secured in an end-to-end manner by the limiting mechanisms (elastic locking member, elastic fastener, etc.) provided on the slidable component 1, on the slidable component 2 and on the needle base, so as to shield the needle head 4 and prevent the needle head from wounding the operator or the patient. As such, when pulling out the needle head, it not only ensures safety, but also avoids pain caused by sudden retraction of the needle head in prior art.

Furthermore, in the unfolding process of the slidable component 1 and the slidable component 2, the needle head 4 is required to be kept as close as possible to the skin of the patient, therefore, if the diameters of the slidable component 1 and the slidable component 2 are too large, such requirement cannot be met. By providing the smooth planar surface 23 on the slidable component 2, the needle head 4 can be placed close to the skin in the unfolding process of the slidable component 1 and the slidable component 2. By providing the notch 28 at a position where the smooth planar surface 23 extends close to the axial line of the needle head, the requirement of the needle head being close to the skin can be further met, thereby alleviating the pain suffered by the patient.

Furthermore, protrusions and annular stopper rings 36 are provided as stopper members 16 and 36 on the slidable component 1 and the needle base, wherein, annular stopper rings 36 are respectively provided on an exterior wall of one end of the needle base close to the needle tip and on an exterior wall of one end of the slidable component 1 close to the needle tip, two protrusions are respectively provided on an interior wall of one end of the slidable component 1 close to the hose and on an interior wall of one end of the slidable component 2 close to the hose, so that the two protrusions on the interior walls of the first and second slidable components are clamped on the annular stopper rings 36 after unfolding, thereby preventing the slidable component 1 or the slidable component 2 from sliding off under a pulling force after the groove is engaged with the elastic fastener.

Although specific embodiments of the present invention are described above, those skilled in the art should understand, this is only illustration, and the protection scope of the present invention is defined by the appended claims. On the premise of not deviating from the principle and essence of the present invention, those skilled in the art can make various changes and modifications to these implementing embodiments. For example, the buckle structure such as the elastic fasteners and grooves may not be used, and instead the slidable components may be secured on the needle base by mutual clamping of elastic washers. These changes and modifications are all embraced within the protection scope of the present invention.

The invention claimed is:
1. A disposable safe vein transfusion puncture needle, comprising
   a needle head,
   a needle base,
   a needle sheath, sleeved on the needle head; and
   a hose, communicated with the needle base,
characterized in further comprising
   a plurality of slidable components; and
   a plurality of limiting mechanisms,
   wherein,
   the needle base is in a tubular shape, with one end stationary and communicated with the needle head and the other end connected to the hose;
   each of the slidable components is in a tubular shape and has two open ends, the plurality of slidable components are sleeved on one another, the innermost slidable component is movably sleeved onto the needle base, and a sum of lengths of the plurality of slidable components in a moving direction is longer than the length of the needle head;
   the limiting mechanisms are disposed on the plurality of slidable components as well as on the needle base and adapted for securing the innermost slidable component to the needle base as well as securing the plurality of slidable components to one another when the plurality of slidable components slide to completely shield the needle head,
   the plurality of slidable components comprise a first slidable component movably sleeved on the needle base and a second slidable component movably sleeved on the first slidable component,
   the limiting mechanisms comprise two elastic fasteners and four grooves, one of the elastic fasteners is disposed on the first slidable component, and the other elastic fastener is disposed on the second slidable component; two of the grooves are disposed on the needle base, and the other two grooves are circumferentially disposed on an exterior wall of the first slidable component; the elastic fasteners and the grooves are adapted for engaging with each other when the first slidable component and the second slidable component slide to completely shield the needle head or when the needle head is completely exposed, so as to limit the movement of the first slidable component and the second slidable component,
   one end of the second slidable component close to the hose has a smooth projection portion circumferentially disposed thereon,
   a smooth planar surface is disposed on a lateral side of the second slidable component, and the plane of the smooth planar surface forms an angle of 5°-20° with an axial line of the needle head; the second slidable component has a notch disposed on the lateral side with the smooth planar surface, and the notch is in a plane parallel to an axial line of the needle head; one end of the notch extends to an open end of the second slidable component away from the hose, and the other end of the notch extends to intersect with the smooth planar surface.

2. The disposable safe vein transfusion puncture needle in accordance with claim 1, characterized in that, the first slidable component also has an elastic locking member adapted for stretching out to prevent the second slidable component from sliding back towards the hose when the first slidable component and the second slidable component slide to completely shield the needle head.

3. The disposable safe vein transfusion puncture needle in accordance with claim 2, characterized in further comprising a handle, wherein, the second slidable component is provided with at least one antiskid area thereon;
   the slidable components are made of elastic material, the elastic fastener is integrally formed in one piece with the slidable component, and the grooves are integrally formed in one piece with the needle base;
   the handle is secured to one end of the needle base connected to the hose;
   the limiting mechanisms further comprise at least one stopper member disposed on the first slidable component or the needle base, adapted for preventing the second slidable component or the first slidable component from sliding off under a pulling force after the groove is engaged with the elastic fastener.

4. The disposable safe vein transfusion puncture needle in accordance with claim 1, characterized in that, the notch is located at a preset distance from an axial line of the needle head.

5. The disposable safe vein transfusion puncture needle in accordance with claim 4, characterized in further comprising a handle, wherein, the second slidable component is provided with at least one antiskid area thereon;
   the slidable components are made of elastic material, the elastic fastener is integrally formed in one piece with the slidable component, and the grooves are integrally formed in one piece with the needle base;

the handle is secured to one end of the needle base connected to the hose;

the limiting mechanisms further comprise at least one stopper member disposed on the first slidable component or the needle base, adapted for preventing the second slidable component or the first slidable component from sliding off under a pulling force after the groove is engaged with the elastic fastener.

6. The disposable safe vein transfusion puncture needle in accordance with claim 1, characterized in further comprising a handle, wherein, the second slidable component is provided with at least one antiskid area thereon;

the slidable components are made of elastic material, one of the two elastic fasteners is integrally formed in one piece with the first slidable component, the other of the two elastic fasteners is integrally formed in one piece with the second slidable component, and the grooves are integrally formed in one piece with the needle base;

the handle is secured to one end of the needle base connected to the hose;

the limiting mechanisms further comprise at least one stopper member disposed on the first slidable component or the needle base, adapted for preventing the second slidable component or the first slidable component from sliding off under a pulling force after the groove is engaged with the elastic fastener.

\* \* \* \* \*